United States Patent [19]

Dowd et al.

[11] Patent Number: 4,714,777
[45] Date of Patent: Dec. 22, 1987

[54] CYCLOPROPANONE HYDRATE DERIVATIVES

[75] Inventors: Paul Dowd, Pittsburgh; Christopher Kaufman, Dravosburg, both of Pa.; Robert H. Abeles, Newton Centre, Mass.

[73] Assignee: University of Pittsburgh, Pittsburgh, Pa.

[21] Appl. No.: 817,762

[22] Filed: Jan. 6, 1986

Related U.S. Application Data

[63] Continuation of Ser. No. 622,841, Jun. 21, 1984, abandoned.

[51] Int. Cl.$^4$ ............................................. C07C 61/04
[52] U.S. Cl. ................................... 562/506; 514/450;
514/519; 514/531; 514/538; 514/572; 514/659;
514/706; 514/729; 549/333; 549/336; 558/434;
560/41; 560/124; 560/173; 560/231; 564/453;
564/455; 564/454; 568/62; 568/700; 568/807
[58] Field of Search ............... 562/506; 560/124, 173;
549/333, 336; 564/453, 454, 455; 568/800, 807,
62

[56] References Cited

PUBLICATIONS

Dowd, J. Am. Chem. Soc., 106, pp. 2703-2704 (1984).
Rousseau, Tetrahedron Letters, 24, pp. 1251-1254 (1983).
Wiseman, Biochemistry, 18, pp. 427-435 (1979).
Wiseman, Biochemistry, 19, pp. 4222-4231 (1980).
Wiseman, J. Biol. Chem., 257, pp. 6328-6332 (1982).

Burger, "Medicinal Chemistry", Part I, 3rd ed., pp. 196-228 (1970).

Primary Examiner—Michael L. Shippen
Attorney, Agent, or Firm—Reed Smith Shaw & McClay

[57] ABSTRACT

The subject invention relates to novel cyclopropanone hydrate derivatives of the structural formula

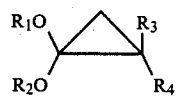

wherein
$R_1$ and $R_2$ are selected from the group consisting of —H, —(CH$_2$)$_n$— where n is an integer between 1 and 20, preferably 2 and 10, —COCH$_2$NH$_2$, and

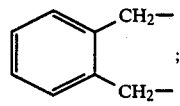

and
$R_3$ and $R_4$ selected from the group consisting of —H, —OH, 13 NH$_2$, —CN, —COOR$_5$, —COOH, —SH, —(CH$_2$)$_n$OH, —(CH$_2$)$_n$NH$_2$, —(CH$_2$)$_n$COOH, —(CH$_2$)$_n$COOR$_5$, —CCH$_3$OH (CH$_2$)$_n$COOH, halogen and C$_7$–C$_{10}$ arakyls, where n is an integer between 1 and 20, preferably 1 and 10, and R$_5$ is an alkyl radical having between 1 and 20, preferably 1 and 10, carbon atoms; and to a process for the synthesis thereof.

1 Claim, No Drawings

CYCLOPROPANONE HYDRATE DERIVATIVES

ACKNOWLEDGEMENT

The invention described herein was made during the course of work under Grant GM27667 from the National Instutes of Health.

This is a continuation of co-pending application Ser. No. 622,841, filed on June 12, 1984.

FIELD OF THE INVENTION

The present invention relates to cyclopropanone derivatives in general, and to cyclopropanone hydrate derivatives specifically and to a process for their synthesis.

BACKGROUND OF THE INVENTION

Cyclopropanone (I) is a very reactive reactive ketone.

I

It is so reactive that it can only be detected at low temperatures in the strict absence of water and other hydroxylic substances. However, the enormous reactivity of cyclopropanone toward water, alcohols, thiols, amines, and other nucleophiles is a key to its potential utility. Stated in terms of chemical equilibria: the adducts of cyclopropanone with nucleophiles are very strongly favored over uncomplexed cyclopropanone. Equations 1–4 provide examples of such favored adducts.

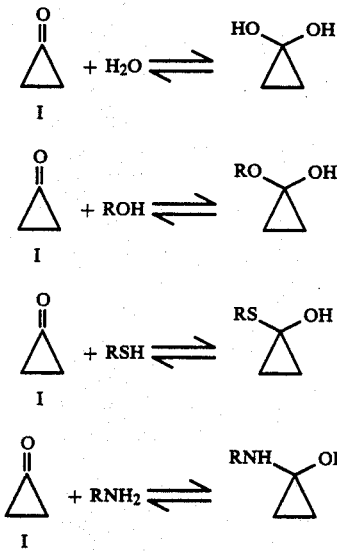

J. S. Wiseman and R. H. Abeles have reported in the article "The Mechanism of Inhibition of Aldehyde Dehydrogenase by Cyclopropanone Hydrate and the Mushroom Toxin Coprine", Biochemistry 18 (1979) 427–435, the potential of cyclopropanone as an enzyme inhibitor and of coprine (II), a naturally-occurring adduct of cyclopropanone with the amide group of glutamine.

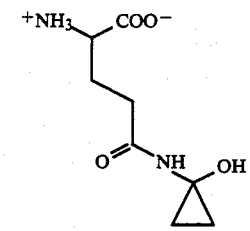

Coprine is a potent inhibitor of the enzyme, alcohol dehydrogenase.

Wiseman and Abeles hypothesized that the inhibition results from the release of cyclopropanone, which reacts with a sulfhydryl group at the active site of the enzyme, thereby inhibiting the enzyme.

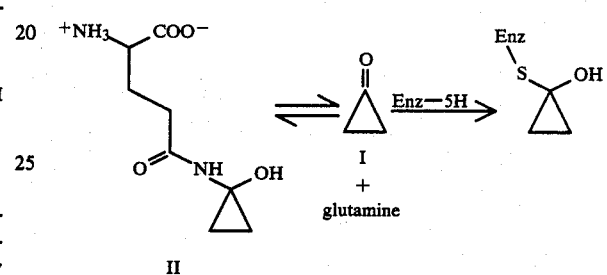

They then report demonstrating experimentally the inhibitory power of cyclopropanone with alcohol dehydrogenase and with other enzymes.

If cyclopropanone could be systematically controlled and synthesized, it could provide a mechanism for converting many enzyme substrates into potent and highly specific inhibitors. The list of substrates could include steriods, peptides, alkaloids, prostaglandins, and other physiologically active substances.

Assuming the proper cyclopropanone derivative could be prepared and attached to a substrate, one would have a new substance with the inhibitory potential of cyclopropanone and, in favorable instances, with the specificity associated with the natural substrate. However, a problem now exists in that synthesis in the cyclopropane area is in a very rudimentary state even though the prior art discloses a variety of cyclopropanone derivatives and processes for their production, e.g., U.S. Pat. No. Re. 27,592; U.S. Pat. No. 2,815,362; U.S. Pat. No. 2,967,181; U.S. Pat. No. 3,047,611; U.S. Pat. No. 3,156,722; U.S. Pat. No. 3,184,509; U.S. Pat. No. 3,341,66; U.S. Pat. No. 3,335,481; U.S. Pat. No. 3,462,491; U.S. Pat. No. 3,711,547; U.S. Pat. No. 3,711,548; U.S. Pat. No. 3,728,388; U.S. Pat. No. 4,076,840; U.S. Pat. No. 4,264,527; and Russian Pat. No. 524,788. O. Pelletier and K. Jankowski, Can. J. Chem., 60, 2383 (1982), disclose the synthesis of a cyclopropanone ketal ester from a copper sulfate catalyzed reaction of ethyl diazoacetate with 1,1-diethoxyprop-1-ene. The reported properties of the synthesized ester are suspect and could not be verified.

Among the most desirable molecules for attachment to enzyme substrates are the protected cyclopropanones identified below as structures III, IV, and V. A synthetic approach to this series might make use of the readily available ethyl diazoacetate (VI)

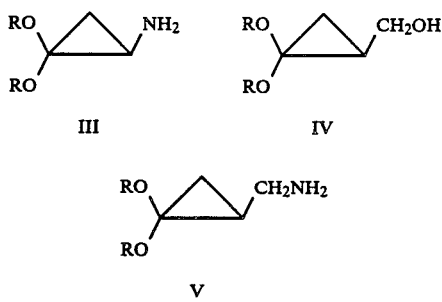

III    IV

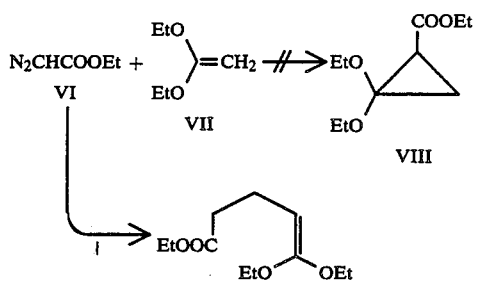

V and diethyl ketene acetal (VII) to prepare the precursor ester (VIII).

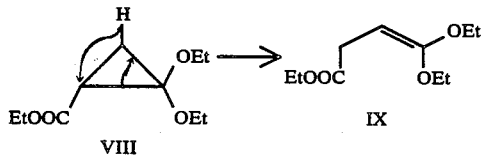

This conventional approach fails to yield the desired precursor ester VIII and instead yields an open product IX which is reported by M. F. Dull and P. G. Abend in "The Reaction of Some Methylene Derivatives with Ketane Diethylacetal", *J. Am. Chem. Soc.* 81 (1959), 2588. The reason for the failure is not known. Possibly the reaction between compound VI and compound VII might yield compound VIII, but compound VIII is unstable and decomposes to compoud IX by a hydrogen transfer reaction, as shown below.

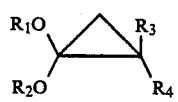

It might be possible to circumvent the rearrangement of configuration VIII to IX by controlling the architecture of the product. Using this concept, it has now surprisingly and unexpectedly been found that the cyclopropanone ketal esters, and other derivatives of cyclopropanone can be successfully synthesized. Such derivatives can be used as chemical intermediates and demonstrate different degrees of effectiveness as biological inhibitors.

SUMMARY OF THE INVENTION

The subject invention relates to novel cyclopropanone hydrate derivatives of the structural formula

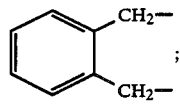

wherein $R_1$ and $R_2$ are selected from the group consisting of —H, —$(CH_2)_n$— where n is an integer between 1 and 20, preferably 2 and 10, —$COCH_2NH_2$, and

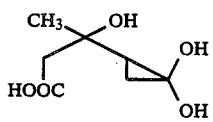

and $R_3$ and $R_4$ are selected from the group consisting of —H, —OH, —$NH_2$, —CN, —$COOR_5$, —COOH, —SH, —$(CH_2)_nOH$, —$(CH_2)_nNH_2$, —$(CH_2)_nCOOH$, —$(CH_2)_nCOOR_5$, —$CCH_3OH(CH_2)_nCOOH$, halogen, and $C_7$–$C_{10}$ aralkyls, where n is an integer between 1 and 20, preferably 1 and 10, and $R_5$ is an alkyl radical having between 1 and 20, preferably 1 and 10, carbon atoms;

and to a process for the synthesis thereof.

In a preferred embodiment, the invention relates to the novel cyclopropanone hydrate derivative cyclomevalonic acid of the structural formula

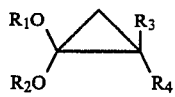

DETAILED DESCRIPTION OF THE INVENTION

The subject invention comprises a novel cyclopropanone hydrate derivative of the structural formula

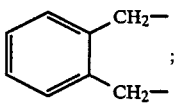

wherein $R_1$ and $R_2$ are selected from the group consisting of hydrogen, —H, —$(CH_2)_n$— where n is an integer between 2 and 20, preferably 2 and 10, —$COCH_2NH_2$, and

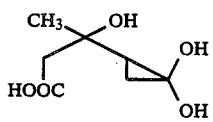

and $R_3$ and $R_4$ are selected from the group consisting of —OH, —$NH_2$, —$COOR_5$, —COOH, —SH, —$(CH_2)_nNH_2$, —$(CH_2)_nCOOH$, —$(CH_2)_nCOOR_5$, —$CCH_3OH(CH_2)_nCOOH$, halogen and $C_7$–$C_{10}$ arakyls, where n is an integer between 1 and 20, preferably 1 and 10, and $R_5$ is an alkyl radical having between 1 and 20, preferably 1 and 10, carbon atoms;

and to a process for the synthesis thereof.

It has now been found that if a cyclic ketene acetal such as X is used, it is possible to successfully prepare cyclopropanone derivatives, such as the cyclopropanone ketal ester XI. More specifically, it has been discovered that reaction of ethyldiazoacetate VI with the cyclic ketene acetal X yields the desired cyclopropanone ketal XI as a moderately stable substance.

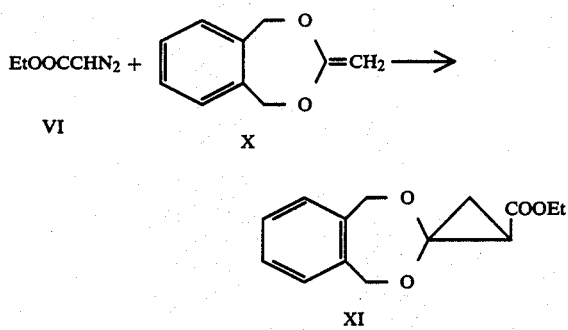

VI    X

XI

The product XI can then be reduced to the carbinol XII. The carbinol XII is attached to substrate(Sub) and the ketal blocking

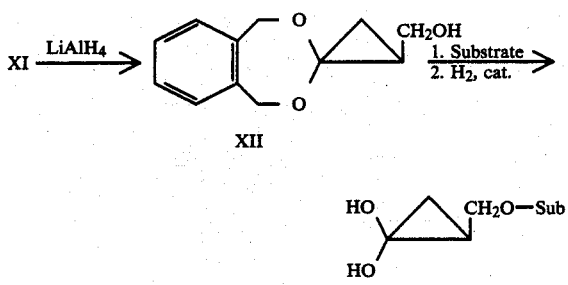

XII

XIII group removed by catalytic hydrogenation to yield the cyclopropanone hydrate, XIII, an enzyme inhibitor.

The ester XI may also be hydrolyzed to the corresponding carboxylic acid XIV. The latter may then be converted by Curtius or Hofmann degradation to the amine XV.

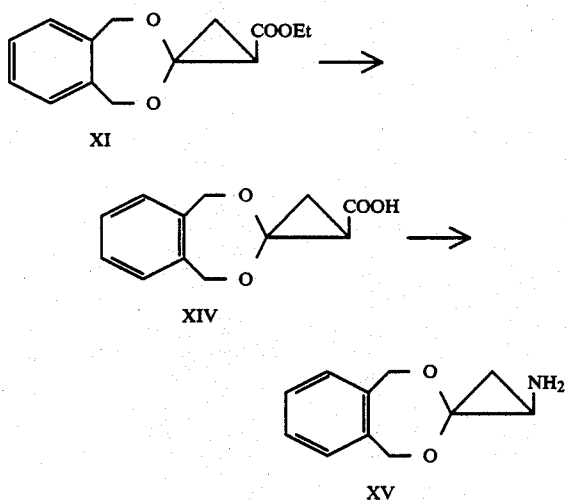

XI

XIV

XV

It has also been found that the amine XVI can be prepared by appropriate reduction of the corresponding nitrile.

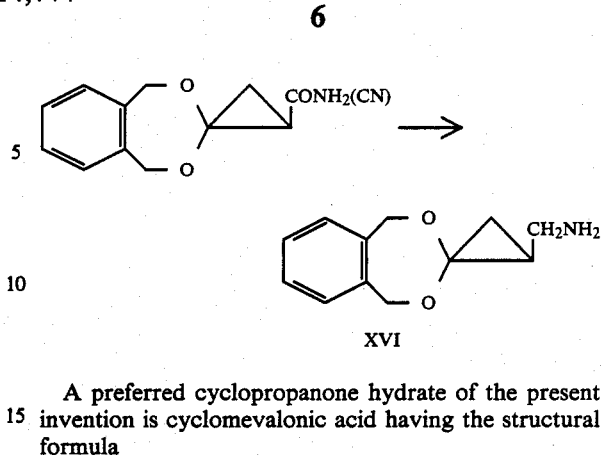

XVI

A preferred cyclopropanone hydrate of the present invention is cyclomevalonic acid having the structural formula

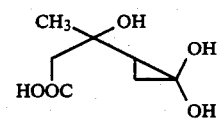

and is prepared using the above synthetic techniques.

Similarly, higher homologues which may have similar effectiveness as biological inhibitors may also be synthesized. The possible reaction sequence for such a synthesis is shown below. The resulting product XVII might be attached to the appropriate enzyme substrate through the carboxyl group.

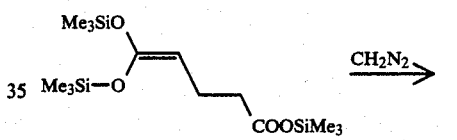

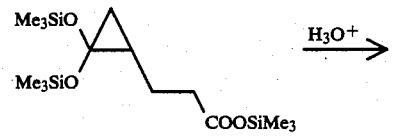

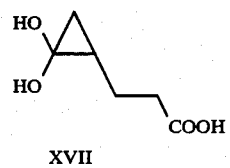

XVII

EXAMPLES

The examples which follow are intended to explain the novel cyclopropanone hydrate derivatives, and the process for their synthesis, in more detail.

Preparation of Ketene Acetal

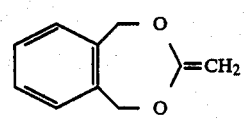

The ketene acetal used as a reactant in Examples 1, 2, 3, 8 and 15 is prepared using the synthesis described by R. Grewe and A. Struve in *Chem. Ber.* 96, 2819 (1963) and incorporated herein by reference.

EXAMPLES

Example 1

Synthesis of 2'-Carbomethoxy-1,5-dihydro-spiro[2,4-benzadioxepin-3,1'-cyclopropane]

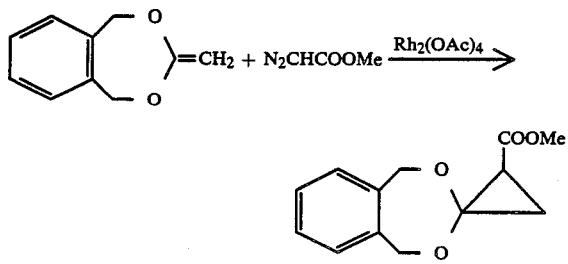

The ketene acetal (1.00 g, 6.17 mmoles) and dirhodium tetraacetate (30 mg, 0.07 mmoles) were placed in a dry 25 mL 3-necked flask containing 10 mL of chloroform. The reaction was cooled to 0° C. and, under an atmosphere of nitrogen, a solution of methyl diazoacetate (648 mg, 6.42 mmoles) in 3 mL of chloroform was added over a period of 7 hours to the green stirring solution. The chloroform was evaporated under reduced pressure and the residue was placed on 100 g of silica gel and eluted with 200 mL of 9:1 hexane-ethyl acetate, 200 mL of 84:15 hexane-ethylacetate, and 800 mL of 8:2 hexane-ethylacetate. A colorless oil (112 mg, 7%) $R_f$ 0.33 (9:1 hexane ethyl acetate), which could be stored at $-15°$ C. but decomposed completely at room temperature in 24 hours, was collected.

The proton NMR (CDCl$_3$) showed: a four proton aromatic multiplet at $\delta$7.2, a two-proton benzylic AB quartet (J=14.0) at $\delta$5.00 and 4.86, a two-proton benzylic AB quartet (J=13.9) at $\delta$4.89 and 4.84, a three-proton methyl singlet, a one-proton cyclopropane doublet of doublets (J=9.5, 6.8) at $\delta$2.2, a one-proton cyclopropane doublet of doublets (J=6.8, 6.0), at 1.8, and a one-proton cyclopropane doublet of doublets (J=9.5, 6.0) at $\delta$1.5.

Example 2

Synthesis of 2'-[2"-2"hydoxypropane)]-1,5-dihydro-spiro[2,4-benzodioxepin-3,1'-cyclopropane]

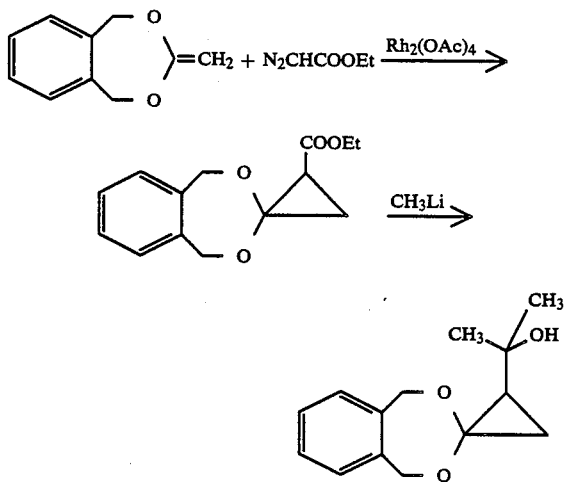

Ketene acetal (500 mg, 3.1 mM) and dirhodium tetracetate (10 mg, 0.02 mM) were placed in a dry 25 mL 3-necked flask with 3 mL of dry chloroform, and cooled to 0° C. Under an atmosphere of nitrogen, a solution of methyl diazoacetate (390 mg, 3.7 mM) in 2 mL of chloroform, was added over 2.5 hours to the cooled, stirred solution. The chloroform was evaporated at 0° C. under reduced pressure. The resulting dark oil was taken up in 3 mL of THF and cooled to $-78°$ C. Nine ml of a 0.95M methyl lithium solution was added, and the reaction was allowed to warm to room temperature and stir for 1.5 hours. The reaction was quenched with 2 mL of water and diluted with 20 mL of ether. The organic layer was washed with four 5 mL portions of water, dried with sodium sulfate, filtered and concentrated under vacuum yielding a light brown oil. This was placed on 60 g of silica gel and eluted with a 65:35 chloroform-ethyl acetate solution. After eluting with 150 mL of solvent, 20 mL fractions were collected. Fractions 7–11 yielded 387 mg (53%) of a white solid, R 0.62 (7:3, hexane-ethyl actate).

The proton NMR spectrum (CDCl) showed: a four-proton aromatic multiplet at $\delta$7.2, a two-proton AB quartet (J=13.9 H$_2$) at $\delta$5.15 and 4.85, a two-proton AB quartet (J=14.1) at $\delta$5.0 and 4.86, a one-proton hydroxyl singlet at $\delta$2.8, a one-proton cyclopropane doublet of doublets (J=11.0, 6.9) at $\delta$1.5, a three-proton methyl singlet at $\delta$1.3, and a one-proton cyclopropane doublet of doublets (J=11.0, 6.0) at $\delta$1.1. The IR spectrum (KBr pellet) showed: 3550 cm$^{-1}$ (M, OH), 2950 cm$^{-1}$ (M, CH), 1015 cm$^1$ (S, COC).

Example 3

Synthesis of 2'-Hydroxymethyl-1,3-dihydro-spiro[2,4-benzodioxepin-3,1'-cyclopropane]

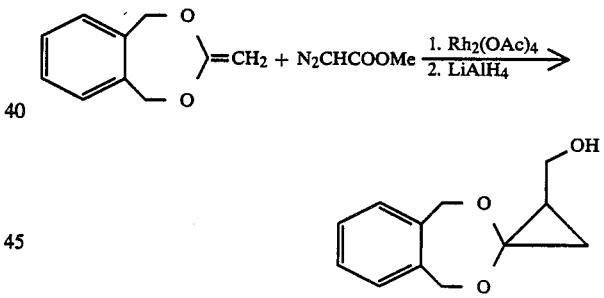

Ketene acetal (14.81 g, 91.4 mmoles) and dirhodium tetraacetate (0.35 g, 0.79 mmols) were placed in a dry 100 mL 3-necked flask with 65 mL of dry chloroform, and cooled to 0° C. Methyl diazoacetate (12.0 g, 118.8 mmoles) was slowly added under an atmosphere of nitrogen over 3.5 hours to the stirred solution, at 0° C. The solvent was evaporated at 0° C. under high vacuum. The resulting black oil was taken up in 100 mL of THF and slowly added under an atmosphere of nitrogen to a flask which was cooled to 0° C. and contained a stirred suspension of 3.6 g of (92.1 mmoles) of LiAlH$_4$ in 300 mL of THF. After warming to room temperature, the excess LiAlH$_4$ was quenched with a saturated sodium sulfate solution. The resulting suspension was diluted to 1000 mL with ether, dried with sodium sulfate, filtered, and concentrated under vacuum yielding a light yellow solid, which was taken up in 25 mL of ether, diluted to 65 mL with benzene and allowed to stand at room temperature for 24 hours. The resulting white crysals, m.p. 68°–69° C. weighed 5.58 g. Another slightly less pure crop weighing 3.867 g, m.p. 67.5°-66° C., was also obtained. The total yield was 50%.

The proton NMR spectrum (CDCl₃) showed: a four-proton aromatic multiplet at $\delta 7.2$, a two-proton benzylic AB quartet (J=14.0) at $\delta 4.99$ and 4.87 a two-proton benzylic AB quartet (J=14.0) at $\delta 4.95$ and 4.85, a one-proton doublet of doublets (J=11.4, J=8.3), at $\delta 3.8$, a one-proton doublet of doublets (J=11.4, J=5.9) at $\delta 3.6$, a broad one-proton hydroxyl singlet at $\delta 2.2$, a one-proton cyclopropane multiplet at $\delta 1.7$, a one-proton cyclopropane doublet of doublets (J=6.1, J=5.9H₃) at $\delta 0.9$. The IR spectrum (KBr pellet) showed: 3300 cm⁻¹ (M, OH), 2850 cm¹ (W, C—H), 1020 cm¹ (S, C—OC). The mass spectrum (70 eV) showed m/e (rel. int.): 206 (0.3, M), 191 (1.6M —CH,), 175 (7, M —CH₂OH), 120 (33, M —C₃H₃O—CH₂OH), 104 (100, C₈H₈). The decoupled ¹³C NMR spectrum (CDCl₃) showed: five aromatic singlets at $\delta 138.9$, 138.7, 127.7, 127.6, 127.5, a cyclopropane quarternary singlet at $\delta 96.1$, two benzylic singlets at $\delta 71.6$, 71.4, a methylene singlet at $\delta 61.9$, a cyclopropane methine singlet at $\delta 21.3$ and a cyclopropane methylene singlet at $\delta 15.7$.

Example 4

Synthesis of 2'-Acetoxymethyl-1,5-dihydro-spiro[2,4-benzodioxepin-3,1'-cyclopropane]

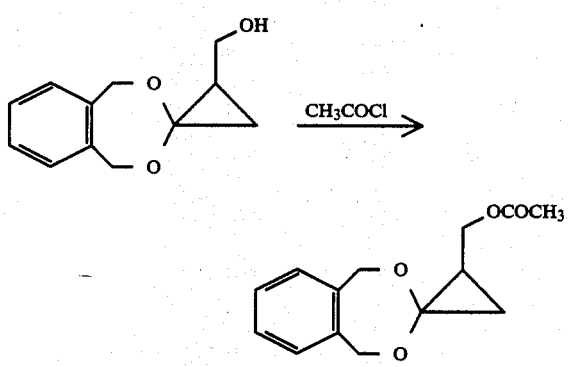

Under an atmosphere of nitrogen, 10 mg (0.13 mmoles) of acetyl chloride was added to a stirred solution of 25 mg (0.12 mmoles) of the alcohol synthesized in Example 3 in 1 mL of dry pyridine. The reaction was allowed to stir for 1 hour. A thin layer chromatogram showed that the reaction was not complete, so an additional 10 mg of acetyl chloride was added. After stirring 10 minutes the solvents were removed under reduced pressure. The resulting white solid was taken up in 1 mL of chloroform and concentrated under reduced pressure. After repeating the chloroform treatment twice, 27 mg (100%) of a white solid, mp 65°-67° C., was obtained, R$_f$ 0.63 (7:3, hexane-ethyl acetate).

The ¹H NMR (CDCl₃) showed: a four proton aromatic multiplet at $\delta 7.2$, a two-proton benzylic AB quartet (J=13.95) at $\delta 4.95$ and 4.87 a two-proton benzylic singlet at $\delta 4.93$, a two-proton doublet of doublets (J=11.6, J=8.6) at $\delta 4.0$ a three proton methyl singlet at $\delta 2.0$, a one proton cyclopropane multiplet at $\delta 1.8$, a one proton cyclopropane doublet of doublets (J=10.3, J=6.1) at $\delta 1.4$ and a one proton cyclopropane doublet of doublets (J=6.1, J=6.2) at $\delta 0.9$. The IR spectrum (KBr pellet) showed: 2850 cm¹ (w, CH), 1715 cm¹ (s, CO). The mass spectrum at 70 eV showed m/e (rel. int.): 205 (0.5M —Ac), 191 (0.8, M —CH—Ac), 175 (7, M —CH, OAc), 120 (24, M —C₂H₂O—CH₂OAc), 104 (100, C₈H₈). Calculated for C₁₂H₁₃O₃: 205.0865. Found: 205.0865.

Example 5

Synthesis of 2-acetoxymethyl-cyclopanone hydrate

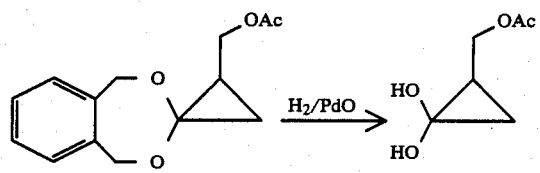

Palladium oxide (10 mg, 0.15 mmoles) was placed in a 25 mL round bottom flask which contained 7 ml of ethyl acetate. The flask was evacuated three times and flushed with hydrogen. After stirring for 15 minutes at room temperature, the resulting black granular palladium suspension was cooled to 0° C., and the ketal (20 mg, 0.08 mmoles) was added. The reaction was followed by the disappearance of starting material using thin layer chromatography, R$_f$ 0.63 (7:3, hexane ethyl acetate). Upon completion (after 30 min), 3 mg of calcium carbonate was added. The reaction was filtered, and concentrated under vacuum to yield 11 mg (93%) of a colorless glass.

The H NMR (CDCl₃) showed: a one-proton doublet of doublets at $\delta 4.2$ (J=11.6, J=5.5), a one-proton doublet of doublets at $\delta 4.0$ (J=11.6, J=9.5), a three proton methyl singlet at $\delta 2.1$, a one proton cyclopropane multiplet at $\delta 1.5$, a one proton cyclopropane doublet of doublets at $\delta 1.2$ (J=10.2, J=5.5), and a one proton cyclopropane doublet of doublets at $\delta 0.7$ (J=5.9, J=5.5). The decoupled ¹³C NMR (CDCl₃) showed five singlets: a carbonyl peak at $\delta 173.3$ a methylene peak at $\delta 8.2$, a methyl peak at 64.5 and three cyclopropane peaks at $\delta 24.7$, 21.5 and 18.2.

Example 6

Synthesis of 2'-N-Acetylphenylalanyl-1,5-dihydrospiro[2,4-benzodioxepin-3,1'-cyclopropane]

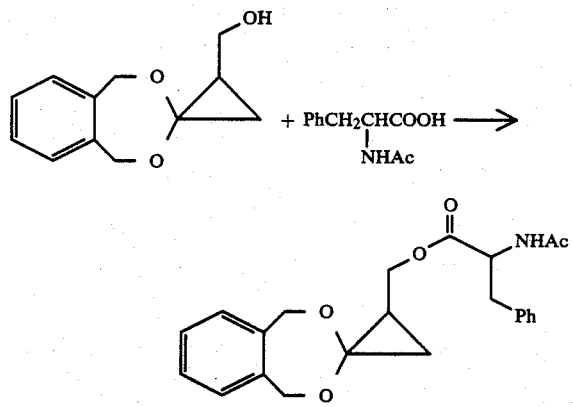

A solution of dicyclohexyldicarbodiimide (110 mg, 0.53 mmoles) in 2 mL of dry methylene chloride was added to a stirred solution of 100 mg (0.49 mmoles) of the alcohol synthesized in Example 3, p-dimethylaminopyridine (60 mg, 0.53 mmoles) and N-acetyl-L-phenyl-alanine (100 mg, 0.49 mmoles) in 6 mL of dry methylene chloride. After stirring for 12 hours at room temperature, the reaction was filtered and concentrated under vacuum. It was then taken up in 10 mL of ethyl acetate, cooled and filtered and washed with two 4 mL portions of a 1M sodium bisulfate solution, two 4 ml portions of water and two 4 ml portions of a 10% sodium bicarbonate solution. The organic layer was dried with sodium sulfate, filtered and concentrated under vacuum. The resulting white foam was taken up in 10 mL of ether and cooled to 0° C. yielding 110 mg (57%) of white crystals, m.p. 78°–80° C. The proton NMR (CCl₃) showed: a nine proton multiplet at δ7.2, a broad one proton amine multiplet at δ5.9, a five proton at δ4.9, a one proton multiplet at δ4.3, a one proton multiplet at δ4.1, a two proton doublet at δ3.1, a three proton methyl singlet at δ2.0, a one proton cyclopropane multiplet at δ1.3 and a one proton cyclopropane multiplet at δ0.9. The IR (KBr pellet) showed: 3400 cm⁻¹ (m, NH), 3300 cm⁻¹ (s, CH), 1720 cm⁻¹ (s, C=O), 1640 cm⁻¹ (s, amide). The mass spectrum at 15 eV showed m/e (rel., int.): 395 (3, M), 353 (2, M —C₂H₂O), 304 (3, M —C₇H₇), 290 (13, M —C₈H₉), 262 (14, M —C₇H₇—C₂H₂O), 189 (71, C₁₂H₁₃O₂), 188 (68, C₁₂H₁₂O₂), 162 (100, C₁₀H₁₀O₂), 147 (53, C₉H₉ON), 120 (49, C₈H₈O), 104 (45, C₈H₈). Calculated for C₁₆H₁₈NO₅: 304.1185. Found 304.1181.

Repeated recrystallization from ether yielded one diastereomer, a white crystalline solid, m.p. 137°–138° C. The ¹H NMR (CDCl₃) showed: a nine-proton aromatic multiplet at δ7.3, a one-proton amide doublet (J=7.5) at δ5.9, a five-proton multiplet consisting of four benzylic protons and one x-amino proton at δ4.9, a one-proton doublet of doublets (J=11.5, J=7.01), at δ4.3, a one-proton doublet of doublets (J=11.5, J=8.4) at δ4.1, a broad two-proton methylene doublet at δ3.13, a three-proton acetate singlet at δ1.96, a one proton cyclopropane methine multiplet at δ1.73, a one proton cyclopropane doublet of doublets (J=5.93, J=10.2) at δ1.3 and a one proton cyclopropane triplet at (J=6.3) δ0.93. The ¹³C NMR (CDCl₃) showed: a carbonyl singlet at δ171, a carbonyl singlet at δ169, aromatic multiplets at δ130, a cyclopropane quartenary singlet at δ95, a benzylic triplet (J=146) at δ73, a methylene triplet (J=146) at δ69, a doublet (J=144) at δ53, a methylene triplet (J=131) at δ37, a cyclopropane methine doublet (J=164) at δ23, a methyl quartet (J=129) at δ23, and a cyclopropane methylene triplet (J=161) at δ17.

Example 7

Synthesis of N-acetylphenylalamine 2,2-dihyldroxy cyclopropylcarbinyl ester

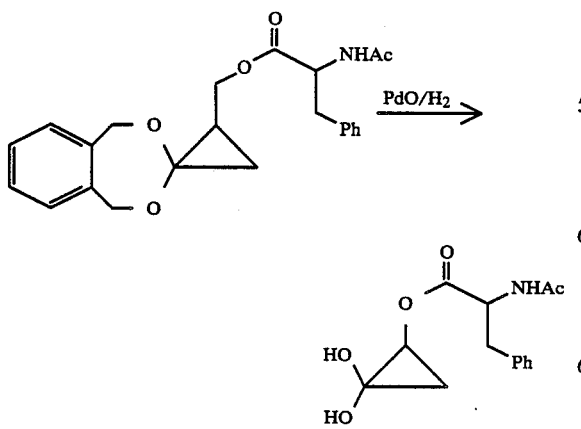

Palladium chloride (10 mg, 0.07 mmoles) was placed in 3 mL of methyl alcohol. The flask was three times evacuated and flushed with hydrogen. After stirring for 5 min at room temperature, the suspension was cooled to 0° C. The ketal (10 mg, 0.08 mmoles) was added and the disappearance of starting material was followed using thin layer chromatography, R/0.63 (7:3, hexane-ethyl acetate). On completion the reaction was quickly filtered and rapidly concentrated under vacuum to yield 7.5 mg (100%) of a colorless oil. The proton NMR (DCDl₃) showed: a one-proton multiplet at δ4.6, a two-proton methylene multiplet at δ4.1, a one-proton doublet of doublets (J=13.7, J=5.7) at 3.1 a one-proton doublet of doublets (J=13.7, J=8.2) at δ3.0 a three-proton methyl singlet at δ1.9, a one-proton cyclopropane multiplet at δ1.4, a one-proton cyclopropane doublet of doublets (J=9.9, J=5.3) at δ1.0, and a one-proton cyclopropane doublet of doublets (J=9.1, J=5.3) at δ0.7.

Example 8

Synthesis of 2',2'-Dibromo-1,5-hydro-spiro[2,4-benzodioxepin-3,1'-cyclopropane]

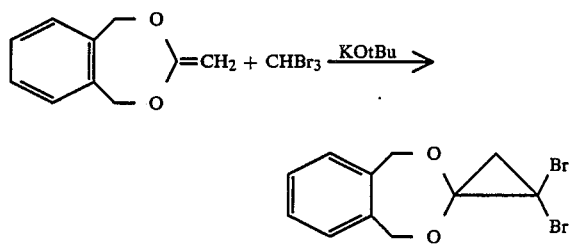

Under an atmosphere of nitrogen 0.962 g (5.93 mmoles) of ketene acetal and 1.33 g (11.8 mmoles) of potassium t-butoxide were placed in 17 mL of pentane and cooled to 0° C. Bromoform (2.99 g, 11.8 mmoles) was added over a period of one hour to the stirred suspension. After stirring an additional hour at 0° C., 20 mL of pentane and 35 mL of chloroform were added. The resulting slurry was poured into a separatory funnel which contained 20 g of water and 10 g of ice. The organic layer was removed and the aqueous phase was washed with three 25 mL portions of chloroform. The combined organic layers were dried with sodium sulfate, filtered and concentrated under vacuum yielding a light brown solid. The solid was taken up in 35 mL of hot ethyl acetate and allowed to cool. The cooled solution yielded 1.258 g of white crystals, m.p. 136°–137° C. Another slightly less pure crop (0.228 g), m.p. 133°–136° C., was also obtained. Total yield 1.486 g (75%). The proton NMR (CDCl₃) showed: a four-proton aromatic multiplet at δ7.2, a four-proton benzylic AB quartet (J$_{AB}$=14.1) at δ5.3 and 4.9, and a two-proton cyclopropane singlet at δ2.1. The mass spectrum at 70 eV showed m/e (rel. int.): 255, 253 (3, M —Br), 213, 211 (3, M —Br—C₂H₂), 185, 183 (12, M —Br—C₃H₂O₂), 104 (100, C₈H₈). Exact mass: Calculated for C₁₁H₁₀O₂⁷⁹Br: 252.9864. Found: 252.9864. Calculated for C₉H₈O⁷⁹Br: 210.9758. Found: 210.9761. Calculated for C₈H₈Br⁷⁹: 182.9809. Found 182.9813.

Example 9

Synthesis of 2'-Bromo-1,5-dihydro-spiro[2,4-benzodioxepin-3,1'-cyclopropane]

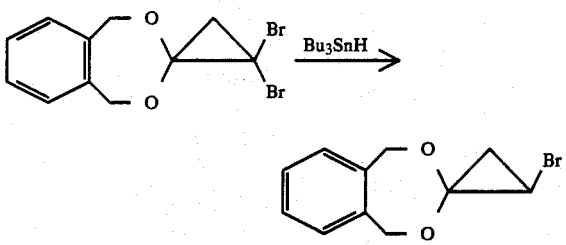

Tri-n-butyltin hydride (4.29 g, 14.7 mmoles) was added under an atmosphere of nitrogen to a stirring solution of 4.27 g (12.8 mmoles) of dibromide in 60 mL of freshly distilled, deoxygenated benzene. After stirring for 18 hours at room temperature, the benzene was evaporated under reduced pressure. The resulting white solid was placed on 400 g of silica gel and eluted with: 400 mL of 1:1 chloroform-hexane, 200 mL of 3:2 chloroform-hexane, 500 mL of 70:30 chloroform-hexane and 1500 mL of 8:2 chloroform-hexane. Two hundred mL-fractions of eluent were collected. After evaporation of the solvents, 3.318 g of white solid was recovered from fractions 9 through 13. Crystallization from 50 mL of pentane yielded 2.258 g (60%) of white crystalline product, m.p. 69°–75° C. Recrystallization from pentane yielded 1.397 g of white solid, m.p. 75°–75.5° C., with no apparent change in the proton NMR.

The proton NMR spectrum (CDCl$_3$) showed: a four-proton aromatic multiplet at $\delta$7.2, a four-proton benzylic multiplet at $\delta$5.0, a one-proton-cyclopropane doublet of doublets (J=9.2, 5.5) at $\delta$3.3, a one-proton cyclopropane doublet of doublets (J=9.2, 7.6) at $\delta$1.78, and a one-proton cyclopropane doublet of doublets (J=7.6, 5.5) at $\delta$1.36. The IR (KBr) showed bands at: 2900 cm$^{-1}$ (w, CH), 1160 cm$^{-1}$ (s, COC), 1060 cm$^{-1}$ (s, COC).

The mass spectrum (15 eV) showed m/e (rel. int.): 184, 182 (11, M —C$_3$H$_4$O$_2$), 175 (22, M —Br), 147 (30, M —Br—CO), 129 (77, M —Br—HCOH), 104 (100, C$_8$H$_8$). Exact mass: calculated for C$_8$H$_7{}^{81}$Br: 183.9711. Found: 183.9810. Calculated for C$_8$H$_8$: 104.0626. Found: 104.0626.

Example 10

Synthesis of Methyl 2,3''-(3'''-hydroxy-3''-methyl propionate) 1,5-dihydrospiro[2,4-benzodioxepin-3,1'-cyclopropane]

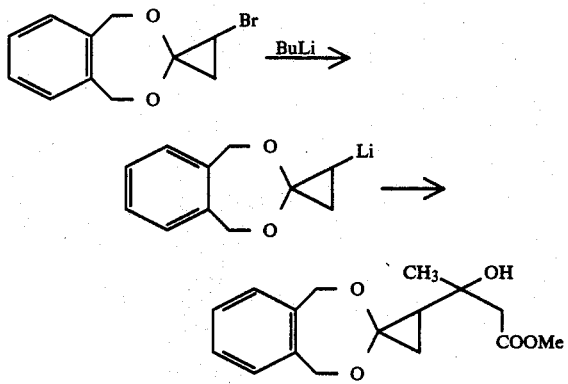

To a solution of 2.00 g (5.98 mmoles) of the monobromide in 80 mL of ether, which was stirring at −78° C. under an atmosphere of nitrogen, 8.0 mL of a 1.2M solution of n-butyl lithium in hexane was added. After stirring for 2.5 hours at −78° C., 1.28 g (7.90 mmoles) of 4,4,4-trimethoxybutan-2-one was added. While, the temperature was maintained at −78° C. and after stirring for 6.5 hours, 10 mL of H$_2$O was added. After standing overnight at −78° C., the reaction was allowed to warm to room temperature. The layers were separated and the aqueous phase was washed with three 10 mL portions of ether. The combined organic layers were then dried with sodium sulfate, filtered and the solvent evaporated. The crude product was chromatographed on 400 g of silica gel and eluted with 400 mL of hexane, 400 mL of 95:5 hexane-ethyl acetate, 400 mL of 90:10 hexane-ethyl acetate, 400 mL of 85:15 hexane-ethyl acetate, 400 mL of 80:20 hexane-ethyl acetate, 400 mL of 75:25 hexane-ethyl acetate, then 70:30 hexane-ethyl acetate yielding, after 1000 mL of the 70:30 hexane-ethyl acetate eluted, pure samples of both diastereomers.

The fast-moving isomer (A), R$_f$0.61 (7:3 hexane-ethyl acetate), a white solid, m.p. 68°–70° C., weighing 177 mg, had the following physical characteristics. The proton NMR (CDCl$_3$) showed: a four-proton aromatic multiplet at $\delta$7.2, a two-proton benzylic AB quartet (J$_{AB}$=13.9) at $\delta$5.1 and 4.8, a two-proton benzylic singlet at $\delta$4.9, a three-proton methyl ester singlet at $\delta$3.6, a one-proton hydroxyl singlet at $\delta$3.2, a two-proton AB quartet (J$_{AB}$=11.2) at $\delta$2.66 and 2.65, a one-proton cyclopropane doublet of doublets (J=7.2, 10.7) at $\delta$1.6, a three-proton methyl singlet at $\delta$1.4, a one-proton cyclopropane doublet of doublets (J=7.2, 5.9) at $\delta$1.3, and a one-proton cyclopropane doublet of doublets (J=5.9, 10.7) at $\delta$1.2. The IR (CDCl$_3$) showed bands at: 3500 cm$^1$ (m, OH), 2925 cm$^1$ (m, CH), 1710 cm$^1$ (s, CO), 1030 cm$^1$ (s, COC). The mass spectrum at 70 eV showed m/e (rel. int.): 277 (0.3, M —CH$_3$), 275 (0.3, M—OH), 201 (0.4, M —H$_2$O—CH$_2$CO$_2$Me), 175 (30, M —(CH$_3$)(OH) CCH$_2$CO$_2$Me), 104 (100, C$_8$H$_8$). Exact mass: calculated for C$_{16}$H$_{19}$O$_4$: 275.1283. Found: 275.1274. Calculated for C$_{15}$H$_{17}$O$_5$: 277.1076. Found: 277.1073.

The slow-moving isomer (B) R$_f$0.58 (7:3 hexane-ethyl acetate), a white solid m.p. 63°–65° C., weighing 127 mg, had the following physical characteristics. The proton NMR (CDCl$_3$) showed: a four-proton aromatic multiplet at $\delta$7.2, a two-proton benzylic AB quartet (J$_{AB}$=13.8) at $\delta$5.11 and 4.82, a two-proton benzylic AB quartet (J$_{AB}$=14.2) at $\delta$4.95 and 4.85, a three-proton methyl ester singlet at $\delta$3.7, a one-proton hydroxyl singlet at $\delta$3.2, a two proton AB quartet (J$_{AB}$=11.1) at 2.59 and 2.58. A one-proton cyclopropane doublet of doublets (J=10.7, 7.3) at $\delta$1.7, a three-proton methyl singlet at $\delta$1.4, a one-proton cyclopropane doublet of doublets (J=7.3, 6.1) at $\delta$1.3, and a one-proton doublet of doublets (J=10.7, 6.1) at $\delta$1.3. The IR (CDCl$_3$) showed bands at 3500 cm$^1$ (m, OH), 2950 cm$^1$ (m, CH), 1720 cm$^1$ (s, CO), 1040 cm$^1$ (s, COC). The mass spectrum at 70 eV showed m/e (rel. int.): 277 (0.4, M —CH$_3$), 275 (0.4, M —OH), 218 (4, M —CH$_3$—CO$_2$Me), 201 (1.3, M —H$_2$O—CH$_2$CO$_2$Me), 175 (24, M —(CH$_3$)(OH)CCH$_2$CO$_2$Me), 104 (100, C$_8$H$_8$). Exact mass: calculated for C$_{15}$H$_{17}$O$_5$: 277.1076. Found: 277.1079. Calculated for C$_{16}$H$_{19}$O$_4$: 275.1283. Found: 275.1276.

The total yield of both diastereomers, including mixed chromatography fractions which were recycled, was 734 mg (42%).

Example 11

Synthesis of 2,3''-(3''-hydroxy-3''-methylpropionic acid)-1,5-dihydrospiro[2,4 benzodioxepin-3,1'-cyclopropane] (Isomer A-Fast Moving Acid)

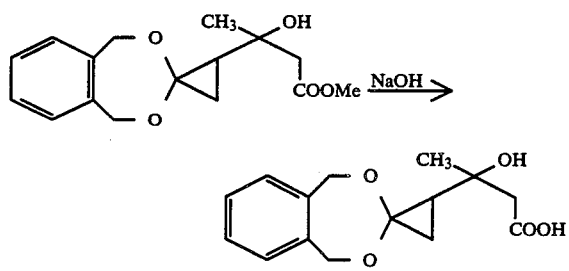

The ester (isomer A, 50 mg, 0.21 mmoles) synthesized in Example 10 was placed in a 50 mL round bottom flask containing 2 mL of methanol. The reaction was cooled to 0° C., and 0.5 mL of 50% NaOH solution was added. The reaction was allowed to stir for 36 hours at 4° C. Evaporation of the solvents yielded a white solid, to which 20 mL of ether and 3 g of ice were added. At 0° C., the aqueous layer was made acidic with concentrated HCl. The organic layer was removed and the aqueous phase was washed quickly with three 10 ml portions of ether. The combined organic layers were dried with sodium sulfate, filtered, and concentrated under vacuum to yield a light yellow solid. The solid residue was taken up in 5 mL of carbon tetrachloride and on cooling to $-15°$ C., 45 mg (77%) of fine white crystals, m.p. 90°–91.5° C., were obtained. The proton NMR spectrum (CDCl$_3$) showed: a four-proton aromatic multiplet at $\delta 7.2$, a two-proton benzylic AB quartet (J=13.8) at $\delta 5.15$ and 4.85, a two-proton benzylic AB quartet (J=14.2) at $\delta 4.95$ and 4.86, a broad hydroxyl singlet at $\delta 4.7$, a two-proton methylene quartet (J=14.8) at $\delta 2.6$ and 2.7, a one-proton cyclopropane doublet of doublets (J=7.3, 6.3) at $\delta 1.6$, and a one-proton cyclopropane doublet of doublets (J=10.7, 6.3), at $\delta 1.25$. The IR spectrum (KBr) showed: 3500 cm$^{-1}$ (m, —OH), 3000 cm$^{-1}$ (m, COOH), 1700 cm$^{-1}$ (s, —COOH). The mass spectrum at 70 eV showed m/e (rel. int.): 175 (40, M —CH$_3$C(OH)COOH), 104 (100, C$_8$H$_8$), 55 (32, C$_3$H$_3$O). Exact mass: Calculated for C$_{11}$H$_{11}$O$_2$: 175.0760.
Found: 175.0759.

Example 12

Synthesis of 2,3''-(3''-hydroxy-3''methylpropionic acid)-1,5-dihydrospiro[2,4-benzodioxepin-3,1'-cyclopropane]

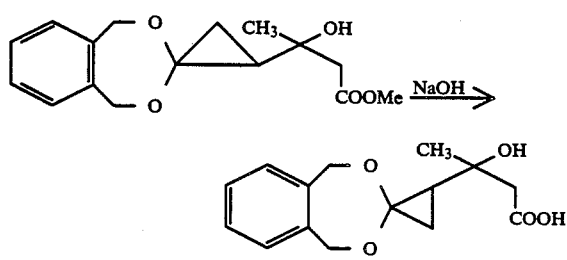

The ester (isomer B, 220 mg, 0.79 mmoles) synthesized in Example 10 was placed in a 100 mL round bottom flask containing 10 mL of methanol, the solution was cooled to 0° C. and 2.5 mL of 50% NaOH was added. The reaction was allowed to stir for 36 hours at 0° C. Evaporation of the solvent yielded a white solid to which 50 mL of ether and 10 g of ice were added. While maintaining the mixture at 0° C. the aqueous layer was made acidic with concentrated HCl. The organic layer was removed and the aqueous phase was washed with three 10 mL portions of ether. The combined organic layers were dried with sodium sulfate, filtered and concentrated yielding a pale yellow solid. The solid residue was taken up in 5 mL of benzene and on concentrating to 2 mL yielded 181 mg (86%) of white crystals of the series B acid, m.p. 105°–107° C.

The proton NMR (CDCl$_3$) showed a four-proton aromatic multiplet at $\delta 7.2$, a four-proton benzylic multiplet at $\delta 5.0$, a broad one-proton hydoxyl singlet at $\delta 3.9$, a two-proton methylene AB quartet (J=15.2) at $\delta 2.6$, a one-proton cyclopropane doublet of doublets (J=10.6, 7.1) at $\delta 1.5$, a three-proton methyl singlet at $\delta 1.5$, a one-proton cyclopropane doublet of doublets (J=7.1, 6.3) at $\delta 1.3$, and a one-proton doublet of doublets (J=10.6, 6.3) at $\delta 1.2$. The IR (KBr pellet) showed: 3500 cm$^1$ (S, OH), 3000 cm$^1$ (M, COOH) and 1700 cm$^1$ (S, C=O).

Example 13

Synthesis of Cyclomevalonic acid (Isomer A)

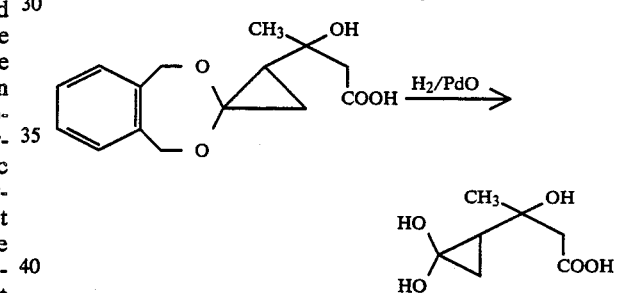

A 10 ml round-bottom flask, which contained a suspension of PdO (13 mg) in 2 mL of ethyl acetate, was evacuated and flushed with hydrogen three times. It was allowed to stir for 1 hour at room temperature then cooled to 0° C. The ketal (10 mg, 0.04 mmoles) synthesized in Example 11 was added and the reaction was followed by the disappearance of starting material at RF 0.53 (0.1% TFA-EtOAc). On completion (65 min), the reaction mixture was filtered, and concentrated under reduced pressure, while being maintained at 0° C., yielding 6 mg (95%) of a colorless glass. The proton NMR (acetone-d$_6$) showed: a two-proton methylene AB quartet at $\delta 2.63$ and 2.65 (J=15.2), a one-proton cyclopropane doublet of doublets at $\delta 1.41$ (J=10.5, 6.8), a three-proton methyl singlet at $\delta 1.3$, a one-proton cyclopropane doublet of doublets at $\delta 1.0$ (J=6.9, 5.4), and a one-proton cyclopropane doublet of doublets at $\delta 0.88$ (J=10.5, 5.4). The mass spectrum at 70 eV showed m/e (rel. int.): 143 (4, M—CH$_3$—H$_2$O), 103 (11, M —C$_3$H$_5$O$_2$), 99 (14, M —CO$_2$—H$_2$O—CH$_3$), 85 (15, C$_4$H$_5$O$_2$), 43 (100, C$_2$H$_3$O). Exact mass: calculated for C$_6$H$_7$O$_4$: 143.0344. Found: 143.0344.

Example 14

Synthesis of Cyclomevalonic Acid (Isomer B)

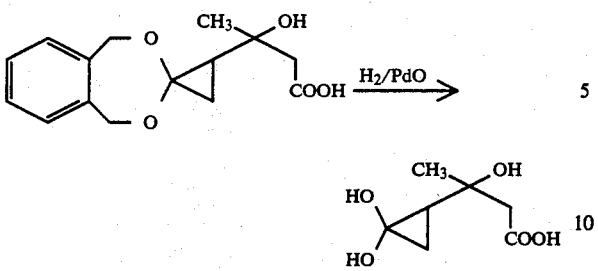

A 10 ml flask containing a suspension of PdO (11 mg) in 1.5 mL of ethyl acetate was evacuated and flushed with hydrogen three times. After stirring for 7.5 hours, the reaction was cooled to 0° C. The ketal (5 mg, 0.02 mmoles) synthesized in Example 12 was added and the reaction was followed by the disappearance of starting material $R_f$0.53 (0.1% TFA-EtOAc). On completion the reaction was filtered and concentrated under reduced pressure, while being maintained at 0° C., yielding 3 mg (100%) of a colorless glass. The proton NMR (acetone-$d_6$) showed: a two-proton singlet at $\delta$2.5, a three-proton methyl singlet at $\delta$1.45, a one-proton cyclopropane doublet of doublets at $\delta$1.4 (J=10.2, 6.8), a one-proton cyclopropane doublet of doublets at $\delta$1.0 (J=6.8, 5.1) and a one-proton cyclopropane doublet of doublets at $\delta$0.8 (J=10.2, 5.1).

Example 15

Synthesis of a Protected Cyclopropanone Hydrate Nitrile

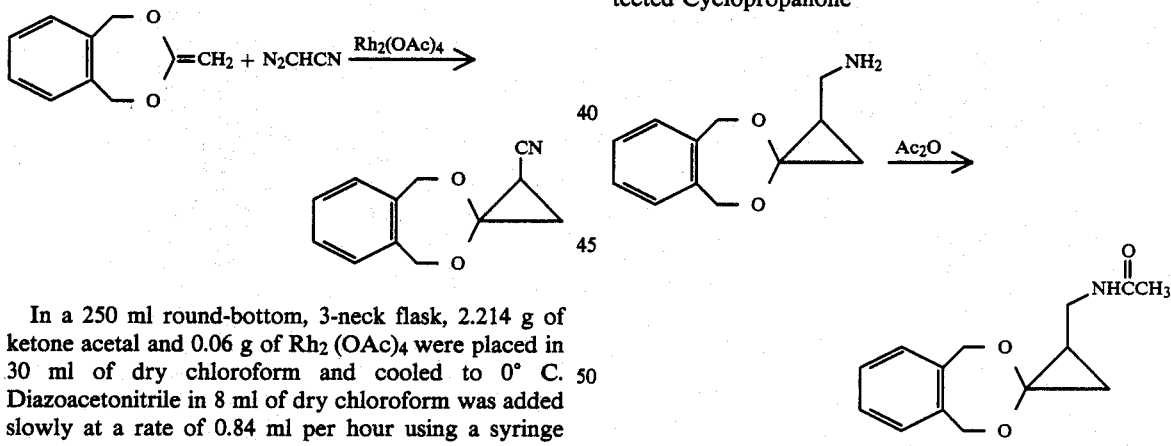

In a 250 ml round-bottom, 3-neck flask, 2.214 g of ketone acetal and 0.06 g of $Rh_2$ $(OAc)_4$ were placed in 30 ml of dry chloroform and cooled to 0° C. Diazoacetonitrile in 8 ml of dry chloroform was added slowly at a rate of 0.84 ml per hour using a syringe pump under an atmosphere of nitrogen. After completion of the addition, the reaction mixture was concentrated on the rotary evaporator yielding a slightly pink-yellow solid. The reaction mixture was dissolved in approximately 40 ml of chloroform and loaded on a 5 g silica gel column. Fractions of 30 ml were collected. The desired product appeared in Fractions 1 and 2. These were combined and crystallized from chloroform-ether. White crystals, mp 133-134, weighing 1.762 g (64%) were obtained. Recrystallization from chloroform-ether yielded 1.379 g with mp 141°-142° C.

Example 16

Synthesis of a Protected Cyclopropanone Hydrate Carbinyl Amine

The nitrile (0.511 g, 0.0025 mol) synthesized in Example 15 and 90 ml of anhydrous ether were placed in a 100 ml round-bottom flask fitted with a reflux condenser. The ether solution was heated to reflux until all the nitrile had dissolved. The solution was cooled to room temperature and 0.290 g of lithium aluminum hydride was added. The reaction mixture was stirred at room temperature for 1 hour. It was then treated with successive portions of 0.24 ml of water, 0.24 ml of 15% sodium hydroxide, and 0.87 ml of water. The resulting granular precipitate was removed by filtration and the filtrate was dried with magnesium sulfate. Evaporation of the ether yielded 0.365 grams (70%) of solid yellow somewhat oily product. This material is somewhat unstable and is usually stored in the deep freeze.

Example 17

Synthesis of a N-Acetyl Carbinyl Amine of the Protected Cyclopropanone

The amine (0.18 g) synthesized in Example 16 and 1 ml of acetic anhydride were placed in a 50 ml round-bottom flask with 1 ml of pyridine. The reaction mixture was stirred at room temperature for 2 hours. It was then poured into 50 ml of chloroform and washed with 20 ml of water. The aqueous solution was extracted with two 50 ml portions of chloroform. The combined chloroform fractions solutions were washed with two 10 ml portions of 10% HCl and a 10 ml portion of saturated sodium bicarbonate solution then dried with magnesium sulfate. Evaporation of the chloroform gave 0.213 g (98%) of an off-color white solid which weighed 0.130 g and which was crystallized from chloroform ether yielding white crystals, mp 121°-122° C.

Example 18

Synthesis of An Adduct of N-Acetyl-L-phenylalanine with the Protected Cyclopropanone Hydrate Carbinyl Amine

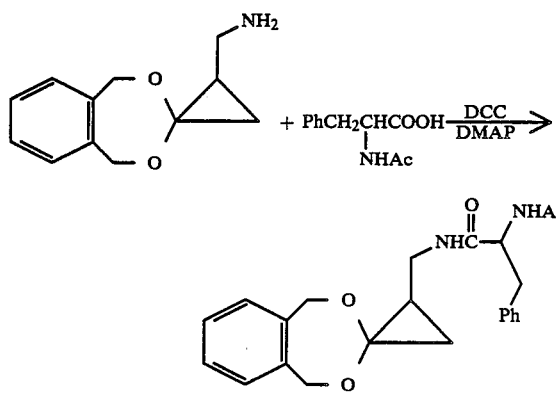

In a 100 ml round-bottom flask was placed 0.215 g of N-acetyl-L-phenylalanine in 110 ml of dry methylene chloride. The amine (0.198 g, 0.965 mmole)) synthesized in Example 16 in 5 ml of dry methylene chloride was added. The solution became somewhat cloudy. To this mixture 4-dimethylaminopyridine (DMAP) was added and the reaction mixture was stirred at room temperature. A solution of dicyclohexylcarbodiimide (DCC) in 5 ml of dry methylene chloride was added and the reaction mixture was stirred at room temperature. After 30 minutes the cloudiness disappeared. The reaction mixture was filtered to remove dicyclohexylurea and the filtrate was evaporated to dryness. The residue was dissolved in ethyl acetate, cooled to $-15°$ and the precipitated dicyclohexylurea was again removed by filtration. The filtrate was washed with 1 ml of potassium bisulfate solution, water, 5% sodium bicarbonate solution and the organic layer was dried with magnesium sulfate and evaporated to dryness. The product was an oily white solid weighing 0.53 g. It consisted of a 50:50 mixture of two diastereomers.

Example 19

Synthesis of 3-[1',1'-Dihydroxycyclopropyl)propionic Acid

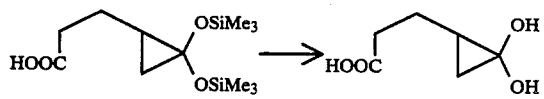

Synthesis of precursor Bis(trimethylsilyl)glutarate

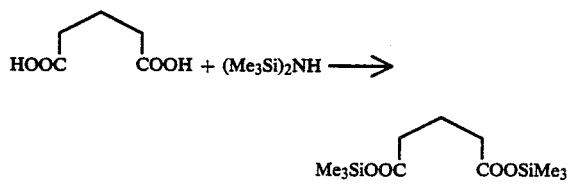

Under an atmosphere of nitrogen, hexamethyldisilazane (40.1 g, 0.24 moles) was slowly added to a stirring solution of glutaric acid (30.0 g, 0.23 moles) in 120 mL of pyridine. After 10 min, chlorotrimethylsilane (13.7 g, 0.13 moles) was added, and reaction was allowed to stir for 2 hours at room temperature, filtered through Celite, and placed under high vacuum overnight. The resulting light green liquid was distilled to yield 60.8 g (95%) of colorless liquid, bp 59°-68° C. at 0.03 mm Hg. The $^1$H NMR (CDCl$_3$) showed: a four-proton triplet (J=7.3) at δ2.3, a two-proton pentuplet (J=7.3) at δ1.9 and an eighteen-proton singlet at δ0.5. The IR spectrum (neat) showed: 2975 cm$^{-1}$ (m, CH), 1720 cm$^{-1}$ (s, CO). The mass spectrum at 70 eV showed m/e (rel. int.): 276 (3, M), 261 (66, M —CH$_3$), 204 (13, M —CH$_2$Si(Me)$_2$), 186 (14, M —HOSi(CH$_3$)$_3$), 147 (100, C$_7$H$_{11}$O$_4$). 73 (89, OSi(CH$_3$)$_3$).

Synthesis of precursor Trimethylsilyl 5,5-Bis(trimethylsiloxy)pen-4-enoic Acid

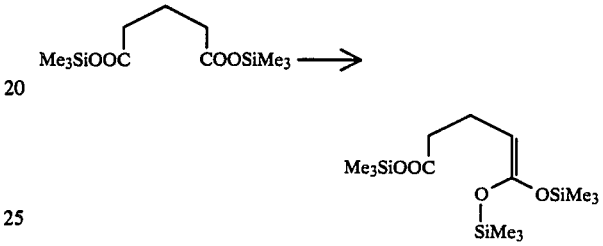

Hexamethyldisilazane (12.3 g, 76.1 mmoles) was placed in a dry, 250 mL, 3-necked flask which contained 100 mL of dry tetrahydrofuran. Under an atmosphere of argon, the stirred solution was cooled to 0° C. and 50.36 mL of n-butyl lithium (1.2M in hexane) was added. The reaction was heated to 45° C. and allowed to stir for 30 min. Upon cooling to room temperature, the resulting hexamethyldisilazide solution was added dropwise under an atmosphere of argon to a flask which had been cooled to $-78°$ C. and contained a solution of bis-trimethylsilyl glutarate (20.0 g, 72.4 mM) in 100 mL of dry tetrahydrofuran. After the reaction had stirred for 30 min. at $-78°$ C., trimethylsilylchloride (11.7 g, 108 mmoles) was added. On warming to room temperature, 300 mL of pentane was added and the resulting milky solution was filtered through Celite. Evaporation of the solvents yielded a green oil which was taken up in 100 mL of pentane. The pentane solution was again filtered through Celite, and concentrated under reduced pressure. The resulting residue was distilled to yield 12.2 g (48%) of a colorless oil, bp 85°-92° C./0.2 mm Hg. The proton NMR (CDCl$_3$) showed: a one-proton vinyl triplet (J=6.9) at δ3.5, a four-proton multiplet at δ2.8, a nine-proton trimethylsilyl ester singlet at δ0.3, and two nine-proton trimethylsilyl acetal singlets at δ0.24 and 0.22. The IR spectrum (neat) showed: 2950 cm$^{-1}$ (m, C—H), 1725 cm$^{-1}$ (s, CO), 1690, 1675 cm$^{-1}$ (s, C=C). The mass spectrum at 70 eV showed m/e (rel. int.): 348 (14, M), 333 (7.3, M—CH$_3$), 231 (7.3, M —CO$_2$SiMe$_3$), 217 (100% M —C$_2$H$_2$O—OSiMe$_3$), 204 (18%, C$_8$H$_2$O—O$_2$Si$_2$).

Synthesis of precursor Trimethylsilyl-3-[1',1'-Bis(-trimethylsiloxy)cyclopropyl]propionate

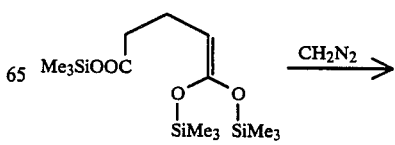

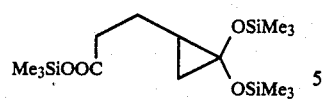

Flask A. To 500 mL of triethylene glycol in a one-liter, three-neck, round-bottom flask protected from the atmosphere by a Drierite drying tube was added 20 g of a 24% suspension of potassium hydride in mineral oil (Alfa). The mixture was stirred vigorously with a magnetic stirrer.

Flask B. In a 100 mL, three-neck, round-bottom flask was placed 30 g of a ketene acetal and 0.07 g of cuprous iodide and a magnetic stirring bar.

Flask A was connected to flask B through a glass tube fitted with a drying tube packed with KOH pellets. One neck of flask A was fitted with a serum cap and a 50 mL syringe loaded with 50 mL of N-nitroso-N-methyl-4-amino-4-methyl-pentanone on a syringe pump was attached to flask through a serum cap. The diazomethane precursor was then added to flask A at a rate of 1.4–2 mL/hr while a stream of argon carried the diazomethane into flask B whose contents were stirred vigorously. A drying tube exit was provided for the gas leaving flask B. A total of 150 mL of the N-nitroso precursor was added to flask A in the course of the reaction over a period of four days.

The reaction was followed using gas chromatography equipped with a glass column packed with 10% SP-2100 on 80/100 Supelcoport. The reaction was run until all the ketene acetal was consumed.

When the reaction was complete it was distilled yielding 5.3 g (13%) of cyclopropane product, bp 68° C./0.007 mm. The major impurity in the reaction is bis-trimethylsilylglutarate which was removed in the forerun.

The proton NMR (CDCl$_3$) of the distilled product showed: a one-proton triplet (J=7.4) at δ2.40, a one-proton triplet (J=7.4) at δ2.39, a one-proton six-line symmetrical multiplet at δ1.8, a one-proton six-line symmetrical multiplet at δ1.5, a two-proton cyclopropane multiplet at δ1.00, and a one-proton cyclopropane triplet at δ0.35. The IR spectrum (neat) showed: 2950 cm$^{-1}$ (s, C—H), 1710 (s, CO) cm$^{-1}$. The mass spectrum at 70 eV showed m/e (rel. int.): 362 (8, M), 347 (5, M —CH$_3$), 231 (37, M —CH$_2$CO$_2$SiMe$_3$), 217 (100, M —CH$_2$CO$_2$SiMe$_3$), 204, (16, M —CH$_2$CO$_2$SiMe$_3$), 55 (30, C$_3$H$_3$O). Exact mass calculated for C$_{15}$H$_{34}$O$_4$Si$_3$: 362.1765. Found: 362.1775.

Synthesis of 3-[1',1'-Bis(trimethylsiloxy)cyclopropyl]propionic Acid

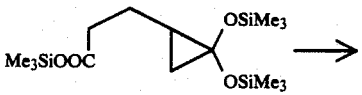

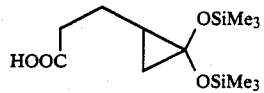

The silyl ester (1 g, 1.76 mmoles) and 10 g of silica gel were placed in a 250 mL round-bottom flask which contained 100 mL of a 0.1% acetic acid-ethyl acetate solution and was immersed in an ice bath. After stirring for 36 hours at 4° C., the silica gel was filtered off and washed with two 40 mL portions of ethyl acetate. The filtrates were combined and concentrated under high vacuum yielding 744 mg (93%) of a colorless oil. The proton NMR (acetone-d$_6$) showed: a two-proton doublet of triplets (J=7.3, 1.0) at δ2.4, a one-proton multiplet at δ1.75, a one-proton multiplet at δ1.55, a one-proton methine multiplet at δ1.15, a one-proton cyclopropane doublet of doublets (J=10.1, 5.5) at δ0.9, and a one-proton cyclopropane doublet of doublets (J=5.76, 5.5) at δ0.4. The infrared spectrum (neat) showed: 3300 cm (w, COOH), 2900 (s, CH), and 1710 (s, CO)cm.$^{-1}$. The mass spectrum at 70 eV showed m/e (rel. int.): 231 (35, M —CH$_2$CO$_2$H), 217 (100, M —OSiMe$_3$), 204 (20, (Me$_3$SiO$_2$)CCH$_2$), 55 (29, C$_3$H$_3$O).

3-[1',1'-dihydroxycyclopropyl)propionic Acid

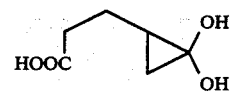

To a suspension of the acid (17 mg, 0.059 mmoles) in 2 in mL of water, acetone (about 0.75 mL) was added until the reaction became homogeneous. Sodium fluoride (20 mg, 0.48 mmoles) was added and the reaction was allowed to stir for 2.5 hours at room temperature. The solvents were removed under reduced pressure. The resulting white solid residue was taken up in 1 mL of D$_2$O and concentrated under vacuum. After repeating the D$_2$O treatment once, a proton NMR spectrum was taken. The proton NMR (D$_2$O) showed: a two-proton triplet (J=7.1) at δ2.1, a two-proton symmetrical multiplet at δ1.4, at one-proton multiplet at δ1.0, a one-proton doublet of doublets (J=10.2, 5.9) at δ0.9, and a one-proton triplet (J=5.9) at δ0.3.

Although the invention has been described in detail for the purposes of illustration, it is to be understood that such detail is solely for that purpose and that variations can be made therein by those skilled in the art without departing from the spirit and scope of the invention except as it may be limited by the claims.

What is claimed is:

1. A cyclopropanone hydrate derivative of the structural formula:

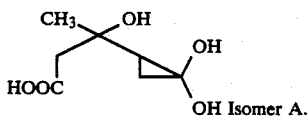

* * * * *

UNITED STATES PATENT AND TRADEMARK OFFICE
CERTIFICATE OF CORRECTION

PATENT NO. : 4,714,777

DATED : December 22, 1987

INVENTOR(S) : Paul Dowd, et al.

It is certified that error appears in the above-identified patent and that said Letters Patent is hereby corrected as shown below: On the title page:

In the Abstract, at line 63, the formula "13NH$_2$" should be -- -NH$_2$ -- ;

In the Abstract, at line 66, the phrase "C$_7$C$_{10}$arakyls" should be -- C$_7$C$_{10}$aralkyls -- ;

At column 1, line 7, the word "Instutes" should be -- Institutes -- ;

At column 1, line 19, the phrase "very reactive reactive ketone" should be -- very active ketone -- ;

At column 2, line 39, the word "steriods" should be -- steroids -- ;

At column 2, line 53, the reference to "No. 3,341,66" should be -- No. 3,341,611 -- ;

At column 3, line 38, the phrase "compoud IX" should be -- compound IX -- ;

At column 4, line 59, the phrase "C$_7$C$_{10}$ara-" should be -- C$_7$C$_{10}$ aral- -- ;

At column 7, line 44, the phrase "[2"-2"hyoxypropane)]" should be -- [2"-2"hydroxypropane)] -- ;

At column 7, line 67, the phrase "racetate" should be -- raacetate -- ;

At column 8, line 20, the word "actate" should be -- acetate -- ;

UNITED STATES PATENT AND TRADEMARK OFFICE
CERTIFICATE OF CORRECTION

PATENT NO. : 4,714,777

DATED : December 22, 1987

INVENTOR(S) : Paul Dowd, et al.

It is certified that error appears in the above-identified patent and that said Letters Patent is hereby corrected as shown below:

At column 8, line 30, the phrase "1015 cm$^1$" should be -- 1015 cm$^{-1}$ -- ;

At column 9, line 13, the phrase "2850 cm$^1$" should be -- 2850 cm$^{-1}$ -- ;

At column 9, line 14, the phrase "1020 cm$^1$" should be -- 1020 cm$^{-1}$ -- ;

At column 9, line 65, the phrase "2850 cm$^1$" should be -- 2950 cm$^{-1}$ -- ;

At column 9, line 65, the phrase "1715 cm$^1$" should be -- 1715 cm$^{-1}$ -- ;

At column 10, line 5, the phrase "cyclopanone" should be -- cyclopropanone -- ;

At column 11, line 3, the phrase "a $^1$M" should be -- a 1M -- ;

At column 12, line 12, the phrase "(DCDl$_3$)" should be -- (CDCl$_3$) -- ;

At column 14, line 23, the phrase "physical characteristics.'" should be -- physical characteristics: -- ;

UNITED STATES PATENT AND TRADEMARK OFFICE
CERTIFICATE OF CORRECTION

PATENT NO. : 4,714,777

DATED : December 22, 1987

INVENTOR(S) : Paul Dowd, et al.

It is certified that error appears in the above-identified patent and that said Letters Patent is hereby corrected as shown below:

At column 21, line 23, the phrase "to flask" should be
-- to flask A --.

Signed and Sealed this

Twenty-seventh Day of December, 1988

Attest:

DONALD J. QUIGG

*Attesting Officer*　　　　　*Commissioner of Patents and Trademarks*